(12) United States Patent
Yang (10) Patent No.: US 10,818,391 B2
(45) Date of Patent: Oct. 27, 2020

(54) SYSTEMS AND METHODS FOR SELECTING A SCANNING DEVICE FOR AN OBJECT

(71) Applicant: SHANGHAI UNITED IMAGING HEALTHCARE CO., LTD., Shanghai (CN)

(72) Inventor: Longzi Yang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 240 days.

(21) Appl. No.: 16/023,295

(22) Filed: Jun. 29, 2018

(65) Prior Publication Data

US 2019/0206552 A1 Jul. 4, 2019

Related U.S. Application Data

(63) Continuation of application No. PCT/CN2017/120310, filed on Dec. 29, 2017.

(51) Int. Cl.
| | |
|---|---|
| G16H 40/20 | (2018.01) |
| G16H 40/67 | (2018.01) |
| G16H 40/63 | (2018.01) |
| G16H 30/20 | (2018.01) |
| G06F 16/23 | (2019.01) |

(52) U.S. Cl.
CPC ............ G16H 40/20 (2018.01); G06F 16/23 (2019.01); G16H 30/20 (2018.01); G16H 40/63 (2018.01); G16H 40/67 (2018.01)

(58) Field of Classification Search
CPC ........ G16H 40/20; G16H 40/67; G16H 40/63; G16H 30/20; G06F 16/23
See application file for complete search history.

(56) References Cited

U.S. PATENT DOCUMENTS

| | | | | |
|---|---|---|---|---|
| 2010/0010345 | A1* | 1/2010 | Shin .................. | A61B 8/00 600/437 |
| 2014/0185740 | A1* | 7/2014 | Chen .................. | A61B 6/545 378/4 |
| 2015/0138245 | A1* | 5/2015 | Lee .................... | G06T 7/11 345/667 |
| 2017/0027530 | A1* | 2/2017 | Heismann ......... | A61B 5/055 |
| 2017/0164915 | A1* | 6/2017 | Li ...................... | A61B 6/037 |
| 2017/0311842 | A1* | 11/2017 | Boettger ........... | A61B 6/0457 |
| 2017/0311921 | A1* | 11/2017 | Feuerlein .......... | A61B 6/481 |

* cited by examiner

*Primary Examiner* — Eliza A Lam
(74) *Attorney, Agent, or Firm* — Metis IP LLC (57) ABSTRACT

A system may include a storage device that stores executable instructions, and at least one processor in communication with the storage device. When executing the executable instructions, the at least one processor may be configured to cause the system to obtain information relating to an object; determine a target operation mode for the object according to the information relating to the object; obtain information relating to previous operations of a plurality of candidate scanning devices from a database; select a target scanning device for the object according to the target operation mode and the information relating to the previous operations of the plurality of candidate scanning devices; and generate a schedule for operating the target scanning device to scan the object.

20 Claims, 7 Drawing Sheets

SYSTEMS AND METHODS FOR SELECTING A SCANNING DEVICE FOR AN OBJECT

CROSS-REFERENCE TO RELATED APPLICATION

This application is a Continuation of International Application No. PCT/CN2017/120310, filed on Dec. 29, 2017, the entire contents of which are hereby incorporated by reference.

TECHNICAL FIELD

The present disclosure generally relates to an imaging system, and more particularly, relates to systems and methods for selecting a scanning device for an object.

BACKGROUND

In a medical imaging system (e.g., a hospital), a plurality of scanning devices (e.g., computed tomography (CT) scanning devices) may be available for operations. For an object (e.g., a patient or a part thereof) to be scanned by one of the scanning devices, it is desirable to provide systems and methods that are capable of scheduling a scanning operation among the scanning devices.

SUMMARY

According to an aspect of the present disclosure, a system is provided. The system may include a storage device that stores executable instructions, and at least one processor in communication with the storage device. When executing the executable instructions, the at least one processor may be configured to cause the system to obtain information relating to an object. The at least one processor may also cause the system to determine a target operation mode for the object according to the information relating to the object. The at least one processor may also cause the system to determine a target operation mode for the object according to the information relating to the object. The at least one processor may also cause the system to obtain information relating to previous operations of a plurality of candidate scanning devices from a database. The database may store information relating to operations performed by the plurality of candidate scanning devices. The at least one processor may also cause the system to select, among the plurality of candidate scanning devices, a target scanning device for the object according to the target operation mode and the information relating to the previous operations of the plurality of candidate scanning devices. The at least one processor may also cause the system to generate a schedule for operating the target scanning device to scan the object. The at least one processor may further cause the system to update, after the target scanning device scans the object, the information relating to operations performed by the target scanning device in the database.

In some embodiments, the at least one processor may further cause the system to determine the target operation mode based on at least one of a target portion of the object to be scanned, a scanning parameter associated with a scanning to be performed on the object, or an image reconstruction parameter associated with a scanning to be performed on the object.

In some embodiments, the at least one processor may further cause the system to obtain information relating to most recent operations of the plurality of candidate scanning devices and select the target scanning device for the object according to the target operation mode and the information relating to the most recent operation of the target scanning device.

In some embodiments, the at least one processor may further cause the system to obtain information relating to a plurality of previous operations of the plurality of candidate scanning device and select the target scanning device for the object according to the target operation mode and the information relating to the plurality of previous operations of the target scanning device.

In some embodiments, the target operation mode may be associated with a CT enhanced scanning or a CT plain scanning.

In some embodiments, the at least one processor may further cause the system to obtain a first plurality of scannings to be performed on the target scanning device and determine, for the first plurality of scannings, a ranking according to which the target scanning device is configured to perform the first plurality of scannings. The first plurality of scannings may include the scanning to be performed on the object associated with the target operation mode.

In some embodiments, the at least one processor may further cause the system to determine the ranking for the first plurality of scannings based on a most recent operation of the target scanning device.

In some embodiments, at least one of the plurality of candidate scanning devices may be configured to perform a second plurality of scannings according to a same gantry rotation time.

According to another aspect of the present disclosure, a method is provided. The method may be implemented on a computing device that includes a storage device and a processor. The method may include obtaining, by the processor, information relating to an object. The method may also include determining, by the processor, a target operation mode for the object according to the information relating to the object. The method may also include obtaining, by the processor, information relating to previous operations of a plurality of candidate scanning devices from a database. The database may store information relating to operations performed by the plurality of candidate scanning devices. The method may also include selecting, by the processor, among the plurality of candidate scanning devices, a target scanning device for the object according to the target operation mode and the information relating to the previous operations of the plurality of candidate scanning devices. The method may also include generating, by the processor, a schedule for operating the target scanning device to scan the object. The method may further include updating, by the processor, after the target scanning device scans the object, the information relating to operations performed by the target scanning device in the database.

According to yet another aspect of the present disclosure, a non-transitory computer readable medium embodying a computer program product is provided. The computer program product may include instructions configured to cause a computing device to obtain information relating to an object. The instructions may also cause the computing device to determine a target operation mode for the object according to the information relating to the object. The instructions may also cause the computing device to obtain information relating to previous operations of a plurality of candidate scanning devices from a database. The database may store information relating to operations performed by the plurality of candidate scanning devices. The instructions may also cause the computing device to select, among the plurality of candidate scanning devices, a target scanning device for the object according to the target operation mode and the information relating to the previous operations of the plurality of candidate scanning devices. The instructions may also cause the computing device to generate a schedule for operating the target scanning device to scan the object. The instructions may also cause the computing device to update, after the target scanning device scans the object, the information relating to operations performed by the target scanning device in the database.

According to yet another aspect of the present disclosure, a system is provided. The system may include an obtaining module configured to obtain information relating to an object, and obtain information relating to previous operations of a plurality of candidate scanning devices from a database. The database may store information relating to operations performed by the plurality of candidate scanning devices. The system may also include a determination module configured to determine a target operation mode for the object according to the information relating to the object. The system may also include a selection module configured to select, among the plurality of candidate scanning devices, a target scanning device for the object according to the target operation mode and the information relating to the previous operations of the plurality of candidate scanning devices. The system may also include a scheduling module configured to generate a schedule for operating the target scanning device to scan the object. The system may further include an updating module configured to update, after the target scanning device scans the object, the information relating to operations performed by the target scanning device in the database.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular exemplary embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," and/or "module" used herein are one method to distinguish different components, elements, parts, section or assembly of different level in ascending order. However, the terms may be displaced by another expression if they achieve the same purpose.

Figure 2:
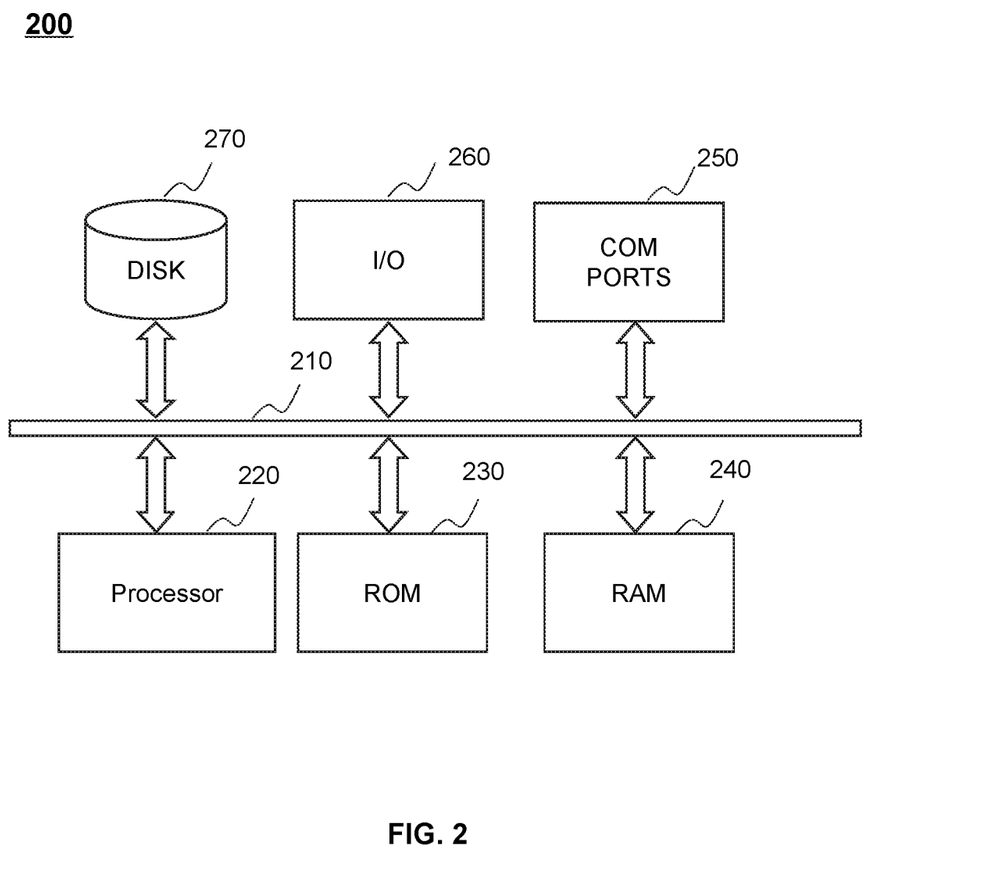
FIG. 2 is a schematic diagram illustrating exemplary hardware and/or software components of a computing device according to some embodiments of the present disclosure.

Generally, the word "module" or "unit" as used herein, refers to logic embodied in hardware or firmware, or to a collection of software instructions. A module or a unit described herein may be implemented as software and/or hardware and may be stored in any type of non-transitory computer-readable medium or another storage device. In some embodiments, a software module/unit may be compiled and linked into an executable program. It will be appreciated that software modules can be callable from other modules/units or from themselves, and/or may be invoked in response to detected events or interrupts. Software modules/units configured for execution on computing devices (e.g., processor 220 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units may be included in connected logic components, such as gates and flip-flops, and/or can be included of programmable units, such as programmable gate arrays or processors. The modules/units or computing device functionality described herein may be implemented as software modules/units, but may be represented in hardware or firmware. In general, the modules/units described herein refer to logical modules/units that may be combined with other modules/units or divided into sub-modules/sub-units despite their physical organization or storage. The description may be applicable to a system, an engine, or a portion thereof.

It will be understood that when a unit, engine or module is referred to as being "on," "connected to," or "coupled to," another unit, engine, or module, it may be directly on, connected or coupled to, or communicate with the other unit, engine, or module, or an intervening unit, engine, or module may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of the present disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

Figure 1:
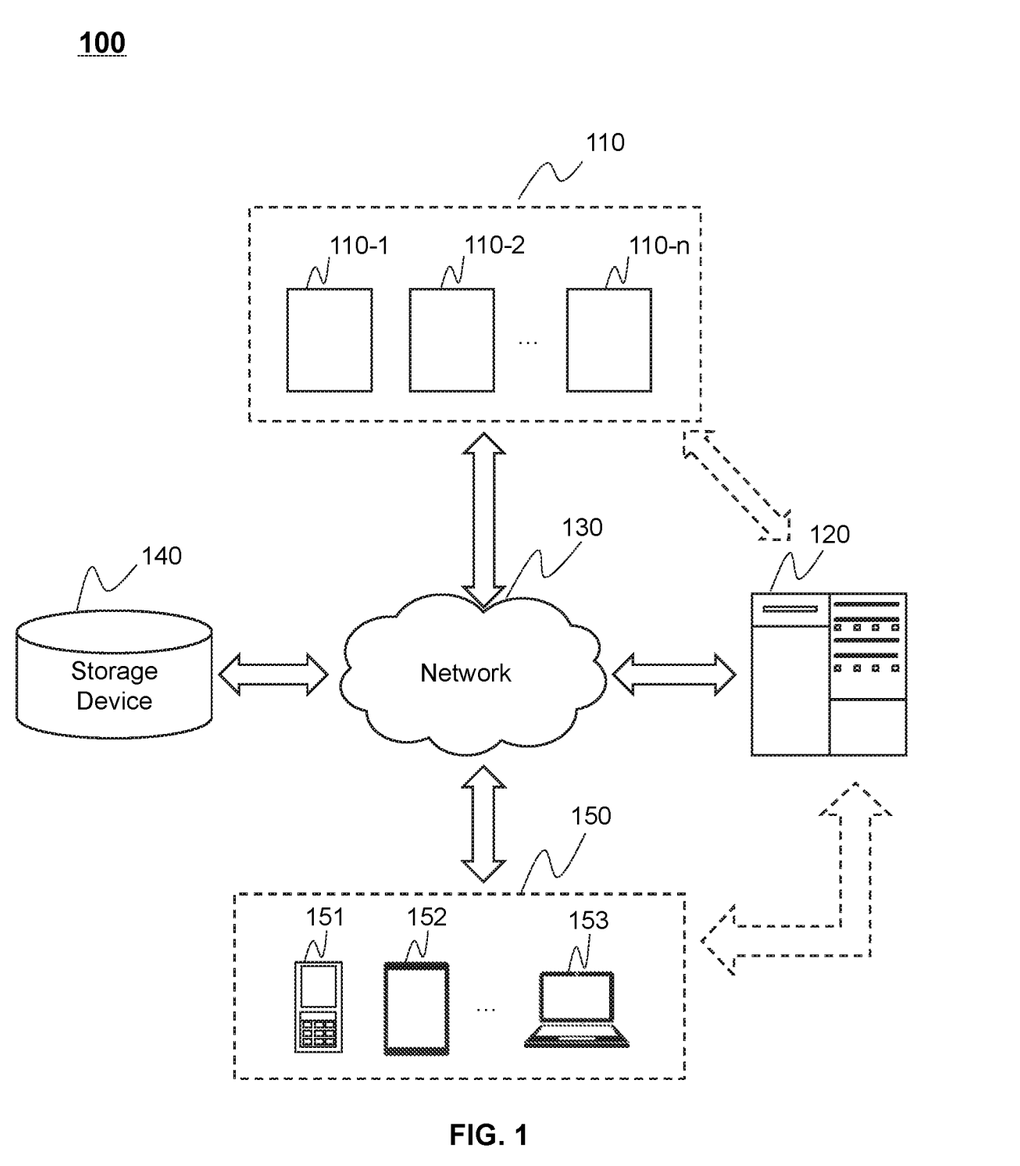
FIG. 1 is a block diagram illustrating an exemplary imaging system according to some embodiments of the present disclosure.

FIG. 1 is a block diagram illustrating an exemplary imaging system 100 according to some embodiments of the present disclosure. In some embodiments, the imaging system 100 may be a single modality imaging system including, for example, a digital subtraction angiography (DSA) system, a magnetic resonance imaging (MRI) system, a computed tomography angiography (CTA) system, a positron emission tomography (PET) system, a single photon emission computed tomography (SPECT) system, a computed tomography (CT) system, a digital radiography (DR) system, etc. In some embodiments, the imaging system 100 may be a multi-modality imaging system including, for example, a positron emission tomography-computed tomography (PET-CT) system, a positron emission tomography-magnetic resonance imaging (PET-MRI) system, a single photon emission computed tomography-positron emission tomography (SPECT-PET) system, a digital subtraction angiography-magnetic resonance imaging (DSA-MRI) system, etc.

As shown in FIG. 1, the imaging system 100 may include one or more scanning devices 110, a processing engine 120, a network 130, a storage device 140, and one or more terminal devices 150. In some embodiments, the scanning device(s) 110, the processing engine 120, the storage device 140, and/or the terminal device(s) 150 may be connected to and/or communicate with each other via a wireless connection (e.g., the network 130), a wired connection, or any combination thereof.

The scanning device(s) 110 may generate or provide image data via scanning an object, or a part of the object. The scanning device(s) 110 may include a plurality of scanning devices (e.g., a scanning device 110-1, a scanning device 110-2, . . . , a scanning device 110-*n*). The plurality of scanning devices may be of same or different modalities. For example, the plurality of scanning devices may be of the same single-modality scanning device, e.g., a CT scanning device. As another example, the plurality of scanning devices may include both a single-modality scanning device and a multi-modality scanning device. In some embodiments, a scanning device (e.g., the scanning device 110-1) may operate in various operation modes. Different operation modes may be used under different conditions (e.g., different objects to be scanned, different requirements with respect to the scanning results). For example, the scanning device 110-1 may operate in a low-dose physical examination mode to deliver the least dosage of radiation toward an object. As another example, the scanning device 110-1 may operate in an emergency operation mode when the least time is used to generate the scanning results. As still another example, the scanning device 110-1 may operate in a coronary heart disease operation mode when a heart region of a patient is to be scanned.

The object being scanned may include a body, substance, or the like, or any combination thereof. In some embodiments, the object may include a specific portion of a body, such as a head, a thorax, an abdomen, or the like, or a combination thereof. In some embodiments, the object may include a specific organ, such as an esophagus, a trachea, a bronchus, a stomach, a gallbladder, a small intestine, a colon, a bladder, a ureter, a uterus, a fallopian tube, etc.

The scanning device(s) 110 may communicate with the processing engine 120, the network 130, the storage device 140, and/or the terminal device(s) 150. For example, the scanning device(s) 110 may transmit the image data to the processing engine 120, the storage device 140, and/or the terminal device(s) 150 via, for example, the network 130. The image data may be sent to the processing engine 120 for further processing or may be stored in the storage device 140. As another example, the scanning device(s) 110 may transmit information relating to a scanning (e.g., scanning parameters) performed on an object to the storage device 140 after the scanning device(s) 110 scans the object.

The processing engine 120 may process data and/or information obtained from the scanning device(s) 110, the storage device 140, and/or the terminal device(s) 150. For example, the processing engine 120 may reconstruct an image (e.g., a CT image) based on the image data obtained from the scanning device(s) 110. Additionally or alternatively, the processing engine 120 may be configured to control the operations of the scanning device(s) 110 (e.g., the operations of the scanning devices 110-1, 110-2, . . . , 110-*n*), the storage device 140, and/or the terminal device(s) 150. For example, the processing engine 120 may schedule the operations of the scanning device(s) 110 when one or more objects need scanning. Specifically, the processing engine 120 may select a scanning device (e.g., the scanning device 110-1) for an object and arrange the time to scan the object by the selected scanning device. In some embodiments, the operations of the scanning device(s) 110 may be scheduled according to the information relating to the object (e.g., the target portion of the object), and/or the operation information of the scanning device(s) 110 (e.g., the most recent operations of the plurality of scanning devices 110-1, 110-2, . . . , 110-*n*).

In some embodiments, the processing engine 120 may be a single server or a server group. The server group may be centralized or distributed. In some embodiments, the processing engine 120 may be local to or remote from one or more other components of the imaging system 100. For example, the processing engine 120 may access information and/or data from the scanning device(s) 110, the storage device 140, and/or the terminal device(s) 150 via the network 130. As another example, the processing engine 120 may be directly connected to the scanning device(s) 110, the storage device 140, and/or the terminal device(s) 150 to access information and/or data. In some embodiments, the processing engine 120 may be implemented on a cloud platform. For example, the cloud platform may include a private cloud, a public cloud, a hybrid cloud, a community cloud, a distributed cloud, an inter-cloud, a multi-cloud, or the like, or any combination thereof.

The network 130 may include any suitable network that can facilitate the exchange of information and/or data for the imaging system 100. In some embodiments, one or more components of the imaging system 100 (e.g., the scanning device(s) 110, the processing engine 120, the storage device 140, and/or the terminal device 150(*s*)) may communicate information and/or data with one or more other components of the imaging system 100 via the network 130. For example, the processing engine 120 may obtain image data from the scanning device(s) 110 via the network 130. As another example, the processing engine 120 may obtain user instructions from the terminal device(s) 150 via the network 130. The network 130 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, or the like, or any combination thereof. For example, the network 130 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 130 may include one or more network access points. For example, the network 130 may include wired and/or wireless network access points such as base stations and/or internet exchange points through which one or more components of the imaging system 100 may be connected to the network 130 to exchange data and/or information.

The storage device 140 may store data, instructions, and/or any other information. In some embodiments, the storage device 140 may store data obtained from the scanning device(s) 110, the processing engine 120 and/or the terminal device(s) 150. In some embodiments, the data stored in the storage device 140 may be organized in a hierarchical manner. For example, the information relating to operations of the scanning device(s) 110 may be stored in a first level, and the information relating to one or more objects being scanned may be stored in a second level. The first level and the second level may be connected through a mapping table that associates the information in the first level with the information in the second level. In some embodiments, the storage device 140 may store data and/or instructions that the processing engine 120 may execute or use to perform exemplary methods described in the present disclosure. In some embodiments, the storage device 140 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 140 may be implemented on a cloud platform as described elsewhere in the disclosure.

In some embodiments, the storage device 140 may be connected to the network 130 to communicate with one or more other components in the imaging system 100 (e.g., the scanning device(s) 110, the processing engine 120, or the terminal device(s) 150). One or more components in the imaging system 100 may access the data or instructions stored in the storage device 140 via the processing engine 120. In some embodiments, the storage device 140 may be part of the processing engine 120.

The terminal device(s) 150 may be connected to and/or communicate with the scanning device(s) 110, the processing engine 120, the network 130, and/or the storage device 140. For example, the processing engine 120 may obtain a scanning protocol from the terminal device(s) 150. As another example, the terminal device(s) 150 may obtain image data from the scanning device(s) 110 and/or the storage device 140. In some embodiments, the terminal device(s) 150 may include a mobile device 151, a tablet computer 152, a laptop computer 153, or the like, or any combination thereof. The mobile device 151 may include a mobile phone, a personal digital assistance (PDA), a gaming device, a navigation device, a point of sale (POS) device, a laptop, a tablet computer, a desktop, or the like, or any combination thereof. In some embodiments, the terminal device(s) 150 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing engine 120 via, for example, a bus, for further processing. Other types of the input device may include a cursor control device, such as a mouse, a trackball, or cursor direction keys. The output device may include a display, a speaker, a printer, or the like, or any combination thereof. In some embodiments, the terminal device(s) 150 may be part of the processing engine 120.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the storage device 140 may be a data storage including cloud computing platforms, such as, public cloud, private cloud, community, hybrid clouds, etc. In some embodiments, the processing engine 120 may be integrated into the scanning device(s) 110. However, those variations and modifications do not depart the scope of the present disclosure.

FIG. 2 is a schematic diagram illustrating exemplary hardware and/or software components of a computing device 200 according to some embodiments of the present disclosure. The processing engine 120 may be implemented on the computing device 200 via its hardware, software program, firmware, or any combination thereof. Although only one such computing device is shown, for convenience, the functions of the processing engine 120 described in the present disclosure may be implemented in a distributed fashion on a number of similar platforms, to distribute the processing load. The computing device 200 may include an internal communication bus 210, a processor 220 (or a CPU), a program storage and data storage of different forms (e.g., a disk 270, a read-only memory (ROM) 230, or a random access memory (RAM) 240), communication (COM) ports 250, and an I/O 260.

The processor 220 may execute program instructions stored in a storage device (e.g., disk 270, ROM 230, RAM 240) to perform one or more functions of the processing engine 120 described in the present disclosure. The processor 220 may include a central processing unit (CPU), an application-specific integrated circuit (ASIC), an application-specific instruction-set processor (ASIP), a graphics processing unit (GPU), a physics processing unit (PPU), a digital signal processor (DSP), a field programmable gate array (FPGA), a programmable logic device (PLD), a microcontroller unit, an advanced RISC machines processor (ARM), or the like, or a combination thereof.

The I/O 260 may input and/or output signals, data, information, etc. In some embodiments, the I/O 260 may enable a user interaction with the processing engine 120. In some embodiments, the I/O 260 may include an input device and an output device. Examples of the input device may include a keyboard, a mouse, a touch screen, a microphone, or the like, or any combination thereof. Examples of the output device may include a display device, a loudspeaker, a printer, a projector, or the like, or any combination thereof. Examples of the display device may include a liquid crystal display (LCD), a light-emitting diode (LED)-based display, a flat panel display, a curved screen, a television device, a cathode ray tube (CRT), a touch screen, or the like, or any combination thereof.

The communication (COM) ports 250 may be connected to a network (e.g., the network 130) to facilitate data communications. The COM ports 250 may establish connections between the scanning device(s) 110, the processing engine 120, the storage device 140, and/or the terminal device(s) 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or any combination thereof. In some embodiments, the COM ports 250 may be and/or include a standardized communication port, such as RS232, RS485, etc. In some embodiments, the COM ports 250 may be a specially designed communication port. For example, the COM ports 250 may be designed in accordance with the digital imaging and communications in medicine (DICOM) protocol.

Figure 3:
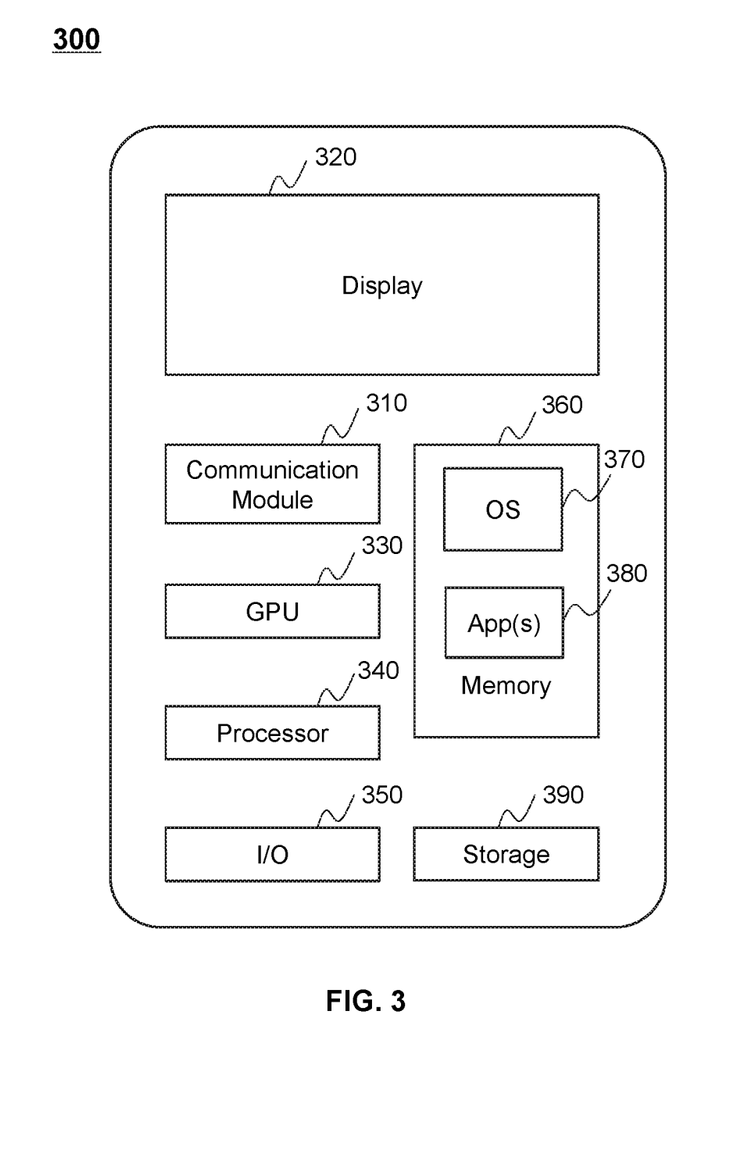
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device 300 according to some embodiments of the present disclosure. In some embodiments, the processing engine 120 and/or the terminal device(s) 150 may be implemented on the mobile device 300 via its hardware, software program, firmware, or any combination thereof. As illustrated in FIG. 3, the mobile device 300 may include a communication module 310, a display 320, a graphic processing unit (GPU) 330, a processor 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the processor 340. The applications 380 may include a browser or any other suitable mobile apps for receiving and rendering information with respect to data processing or other information from the processing engine 120. User interactions with the information stream may be achieved via the I/O 350 and provided to the processing engine 120 and/or other components of the imaging system 100 via the network 130.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or external device. A computer may also act as a server if appropriately programmed.

Figure 4:
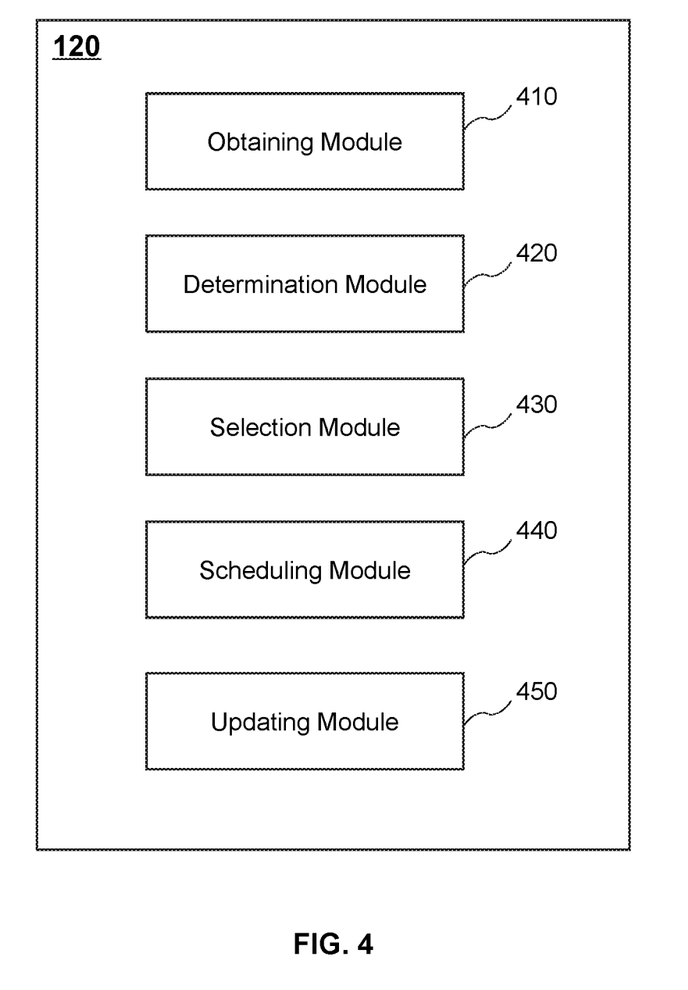
FIG. 4 is a block diagram illustrating an exemplary processing engine according to some embodiments of the present disclosure.

FIG. 4 is a block diagram illustrating an exemplary processing engine 120 according to some embodiments of the present disclosure. The processing engine 120 may include an obtaining module 410, a determination module 420, a selection module 430, a scheduling module 440, and an updating module 450. In some embodiments, the obtaining module 410, the determination module 420, the selection module 430, the scheduling module 440, and/or the updating module 450 may be connected to and/or communicate with each other via a wired connection, a wireless connection, or any combination thereof.

The obtaining module 410 may be configured to obtain information relating to an object. In some embodiments, the object may be a patient and the information relating to the object may include the identification number of the patient, the name of the patient, the gender of the patient, the age of the patient, the weight of the patient, the height of the patient, the historical information (e.g., historical examination information) of the patient, a specific portion of a patient to be scanned, etc. Additionally or alternatively, the information relating to an object may include a scanning protocol of the object. The scanning protocol may include information related to a scanning parameter (e.g., a pitch of a CT scanning) associated with the scanning, and/or an image reconstruction parameter (e.g., a reconstruction algorithm of a CT scanning) associated with the scanning. In some embodiments, the obtaining module 410 may obtain the information relating to the object from the storage device 140, the terminal device(s) 150, a radiology information system (RIS) (not shown) that is connected to or communicated with the imaging system 100, etc. In some embodiments, the obtaining module 410 may obtain the information relating to the object from a user (e.g., a technician, a doctor) via an input device (e.g., a touchscreen, a keyboard).

The obtaining module 410 may also obtain information relating to a previous operation of a scanning device (e.g., the scanning device(s) 110). The previous operation of the scanning device may include an operation that is completed before the scanning device (or the obtaining module 410) obtains information relating to an object to be scanned by the scanning device. The previous operation of the scanning device may also include an operation that is being performed but starts before the scanning device (or the obtaining module 410) obtains the information relating to the object to be scanned by the scanning device. The obtaining module 410 may obtain the information relating to the previous operation of the scanning device from a database. In some embodiments, the database may be implemented in the storage device 140, a storage module of the processing engine 120 (not shown), a storage module of the scanning device(s) 110 (not shown), or an external source.

The obtaining module 410 may also obtain information relating to a plurality of scannings to be performed by a scanning device. Each of the plurality of scannings may correspond to an object to be scanned by the scanning device.

The determination module 420 may be configured to determine a target operation mode for an object according to the information relating to the object. The target operation mode may be an operation mode that is suitable for the object. Merely by way of example, the target operation mode of a scanning device may be an emergency operation mode, a coronary heart disease operation mode, or a low-dose physical examination mode, an operation mode associated with a CT enhanced scanning, an operation mode associated with a CT plain scanning, etc. In some embodiments, the determination module 420 may determine the target operation mode for the object based on, for example, the target portion of the object to be scanned, the scanning protocol of the object, or the like, or a combination thereof.

The selection module 430 may be configured to select, among a plurality of candidate scanning devices (e.g., the scanning devices 110-1, 110-2, . . . , 110-n), a target scanning device for an object according to the target operation mode for the object and the information relating to the previous operations of the plurality of candidate scanning devices. The target scanning device may be a candidate scanning device of which the pervious information matches the target operation mode. In some embodiments, the selection module 430 may select a target scanning device according to the target operation mode and the information relating to the most recent operations of the plurality of candidate scanning devices. In some embodiments, the selection module 430 may select a target scanning device according to the target operation mode and the information relating to the plurality of previous operations of the plurality of candidate scanning devices. Detailed description of the selection of the target scanning device will be found in FIG. 6 and the description thereof.

The scheduling module 440 may be configured to generate a schedule for operating a scanning device (e.g., a target scanning device) to scan an object. The schedule may include a time arrangement or time window in which the scanning device is available or suitable for performing the scanning of the object. In some embodiments, when the scanning device is configured to perform a plurality of scannings on different objects, the scheduling module 440 may generate the schedule based on the urgency degree of each scanning. For example, a heart region of a patient having a heart attack may be scanned by the scanning device with the highest priority.

The scheduling module 440 may also determine a ranking of a plurality of scannings to be performed on a scanning device. The ranking may refer to an order of the plurality of scannings to be performed by the scanning device. In some embodiments, the scheduling module 440 may determine the ranking based on the information relating to the most recent operation of the scanning device. Detailed description of the determination of the ranking will be found in FIG. 7 and the description thereof.

The updating module 450 may be configured to update the information relating to operations performed by a scanning device (e.g., the target scanning device) in a database (e.g., a database implemented in the storage device 140). For example, after the target scanning device scans an object, the updating module 450 may update and/or store the information relating to the operation performed by the target scanning device in the database. In some embodiments, the updating module 450 may immediately update the information in the database after the scanning is completed. In some embodiments, the updating module 450 may periodically update the information in the database according to a schedule (e.g., updating once every two weeks).

In some embodiments, one or more modules illustrated in FIG. 4 may be implemented in at least part of the imaging system 100 as illustrated in FIG. 1. For example, the obtaining module 410, the determination module 420, the selection module 430, the scheduling module 440, and/or the updating module 450 may be integrated into a console (not shown). Via the console, a user may set parameters for scanning an object, controlling imaging processes, controlling parameters for reconstruction of an image, visualizing a virtual scene associated with the object, etc. In some embodiments, the console may be implemented via the processing engine 120 and/or the terminal device(s) 150.

Figure 5:
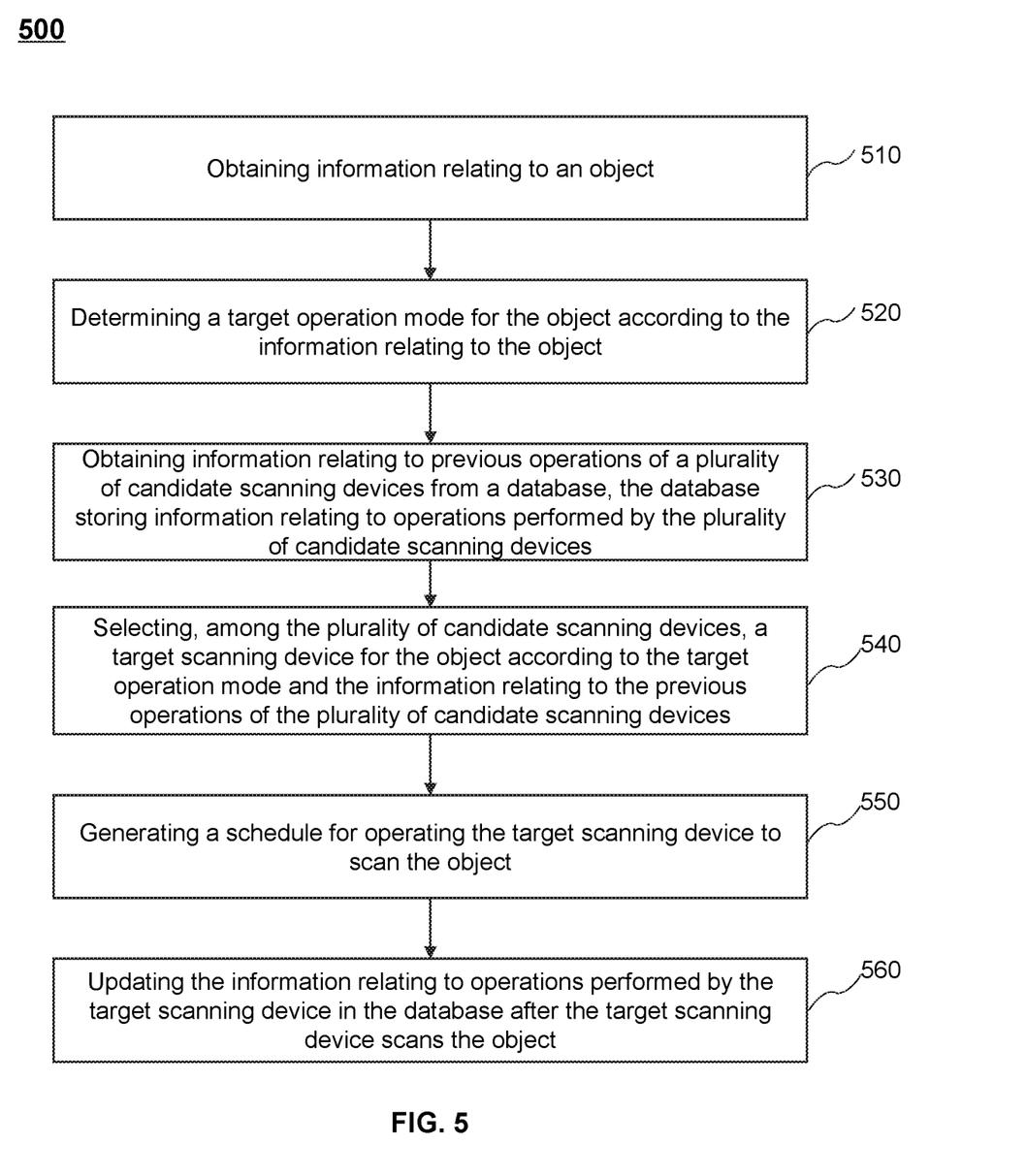
FIG. 5 is a flowchart illustrating an exemplary process for scanning an object according to some embodiments of the present disclosure.

FIG. 5 is a flowchart illustrating an exemplary process 500 for scanning an object according to some embodiments of the present disclosure. In some embodiments, one or more operations of the process 500 illustrated in FIG. 5 may be executed by one or more components of the imaging system 100. For example, the process 500 illustrated in FIG. 5 may be implemented as a set of instructions stored in the storage device 140. The processing engine 120, the processor 220 of the computing device 200 illustrated in FIG. 2, and/or the processor 340 of the mobile device 300 illustrated in FIG. 3 may execute the set of instructions and may accordingly be directed to perform the process 500. For illustration purposes, the implement of the process 500 in the processing engine 120 is described herein as an example. It shall be noted that the process 500 can also be similarly implemented in the processor 220 of the computing device 200 and/or the processor 340 of the mobile device 300.

In 510, the obtaining module 410 may obtain information relating to an object. The object may include substance, tissue, an organ, a specimen, a body, or the like, or any combination thereof. In some embodiments, the object may include a head, a breast, a lung, a pleura, a mediastinum, an abdomen, a long intestine, a small intestine, a bladder, a gallbladder, a triple warmer, a pelvic cavity, a backbone, extremities, a skeleton, a blood vessel, or the like, or any combination thereof. In some embodiments, the obtaining module 410 may obtain the information relating to the object from the storage device 140, the terminal device(s) 150, a radiology information system (RIS) (not shown) that is connected to or communicates with the imaging system 100, etc. In some embodiments, the obtaining module 410 may obtain the information relating to the object by recognizing a barcode associated with the object and obtaining the information associated with the recognized barcode. For example, the obtaining module 410 may include a barcode reader configured to scan the barcode attached to part of the object and obtain the information relating to the object. In some embodiments, the obtaining module 410 may include input devices (e.g., a touchscreen, a keyboard, or a voice input device) (not shown). The information relating to the object may be input by a user (e.g., a technician, a doctor) via the input devices.

In some embodiments, the object may be a patient and the information relating to the patient may include the identification number of the patient, the name of the patient, the gender of the patient, the age of the patient, the weight of the patient, the height of the patient, the historical information (e.g., historical examination information) of the patient, a specific portion of a patient to be scanned, etc. Additionally or alternatively, the information relating to an object may include a scanning protocol of the object. The scanning protocol may include information related to a scanning parameter associated with the scanning, and/or an image reconstruction parameter associated with the scanning. For brevity, a CT scanning is taken as an example in the following description. The scanning parameter may include an X-ray tube voltage (kV), an X-ray tube current (mA), a total exposure time, a scan type (e.g., a helical scan, an axial scan), a scan field of view (FOV), a pitch, a gantry tilt angle, a gantry rotation time, a slice thickness, etc. The image reconstruction parameter may include a reconstruction FOV, a reconstruction slice thickness, a reconstruction interval for image reconstruction, a window width (WW), a window level (WL), a reconstruction matrix, a reconstruction algorithm (e.g., a filtered back projection algorithm, a fan-beam reconstruction algorithm, an iterative reconstruction algorithm), etc. In some embodiments, the scanning protocol may be provided by a doctor or a technician.

In 520, the determination module 420 may determine a target operation mode for the object according to the information relating to the object. For example, the determination module 420 may determine the target operation mode for the object based on, for example, the target portion of the object to be scanned, the scanning protocol of the object, or the like, or a combination thereof. The target operation mode may be an operation mode that is suitable for the object. The target operation mode may be any one of the operation modes of a scanning device (e.g., the scanning device 110-1) as described elsewhere in the disclosure (e.g., the emergency operation mode, the coronary heart disease operation mode, the low-dose physical examination mode).

In some embodiments, the target operation mode may be associated with a CT enhanced scanning or a CT plain scanning. The CT enhanced scanning may refer to a CT scanning on an object which is injected with a contrast medium. The CT plain scanning may refer to a CT scanning on an object which is not injected with a contrast medium. As used herein, the contrast medium may be used to enhance the contrast of structures or fluids within the object in an image. An exemplary contrast medium may include iodine-based compounds, barium-sulfate compounds, etc.

In 530, the obtaining module 410 may obtain information relating to previous operations of a plurality of candidate scanning devices. A candidate scanning device may be a scanning device (e.g., the scanning device(s) 110) that is capable of performing the scanning on the object. For example, the plurality of candidate scanning devices may be the scanning devices 110-1, 110-2, . . . , 110-n as described in connection with FIG. 1. The previous operation of a candidate scanning device may refer to an operation that has been performed or is being performed by the candidate scanning device. For example, an operation that is completed by the scanning device 110-1 before the obtaining module 410 obtains the information relating to the object may be regarded as a previous operation of the scanning device 110-1. As another example, an operation that is being performed but starts before the obtaining module 410 obtains the information relating to the object may also be regarded as a previous operation.

The information relating to the previous operation of a candidate scanning device may include information relating to, for example, the specific portion (e.g., a head, a breast, a lung) of an object scanned by the candidate scanning device, one or more scanning parameters (e.g., kV, mA, scan FOV, etc.) and/or imaging reconstruction parameters (e.g., reconstruction interval, WW, WL) associated with the previous operation. In some embodiments, the information relating to the previous operation of the candidate scanning device may include the information relating to the most recent operation of the candidate scanning device. In some embodiments, the information relating to the previous operation of the candidate scanning device may include the information relating to a plurality of previous operations of the candidate scanning device.

The information relating to the previous operations of the plurality of candidate scanning devices may be obtained from a database storing the information. The database may store information relating to operations performed by the plurality of candidate scanning devices. In some embodiments, the database may be implemented in the storage device 140, a storage module of the processing engine 120 (not shown), a storage module of the scanning device(s) 110 (not shown), or an external source. For example, the obtaining module 410 may obtain the information relating to the previous operations of the plurality of candidate scanning devices from the storage device 140 via, for example, the network 130. In some embodiments, the information relating to the previous operations of a candidate scanning device may be obtained from the database according to a mapping table that indicates a relationship between the information relating to the previous operations and the candidate scanning device. The mapping table may be immediately or periodically updated when a candidate scanning device completes an operation.

In 540, the selection module 430 may select, among the plurality of candidate scanning devices, a target scanning device for the object according to the target operation mode and the information relating to the previous operations of the plurality of candidate scanning devices. The target scanning device may be a candidate scanning device of which the information relating to the previous operation matches the target operation mode.

In some embodiments, the selection module 430 may select a target scanning device according to the target operation mode and the information relating to the most recent operations of the plurality of candidate scanning devices. In some embodiments, the selection module 430 may select a target scanning device according to the target operation mode and the information relating to the plurality of previous operations of the plurality of candidate scanning devices. Detailed description of the selection of the target scanning device will be found in FIG. 6 and the description thereof.

In 550, the scheduling module 440 may generate a schedule for operating the target scanning device to scan the object. The schedule may include a time arrangement or time window in which the target scanning device is available or suitable for performing the scanning of the object. In some embodiments, when the target scanning device is configured to perform a plurality of scannings on different objects, the scheduling module 440 may generate the schedule based on the urgency degree of each scanning. For example, a patient having a heart attack may be scanned by the target scanning device with the highest priority.

In 560, after the target scanning device scans the object, the updating module 450 may update the information relating to operations performed by the target scanning device in the database. For example, after the target scanning device scans the object, the updating module 450 may update and/or store the information relating to the operation performed by the target scanning device on the object in the database. The update of the information may be performed immediately after the scanning is completed or periodically according to a schedule (e.g., updating once every two weeks).

It should be noted that the above description of the process 500 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 560 may be omitted.

Figure 6:
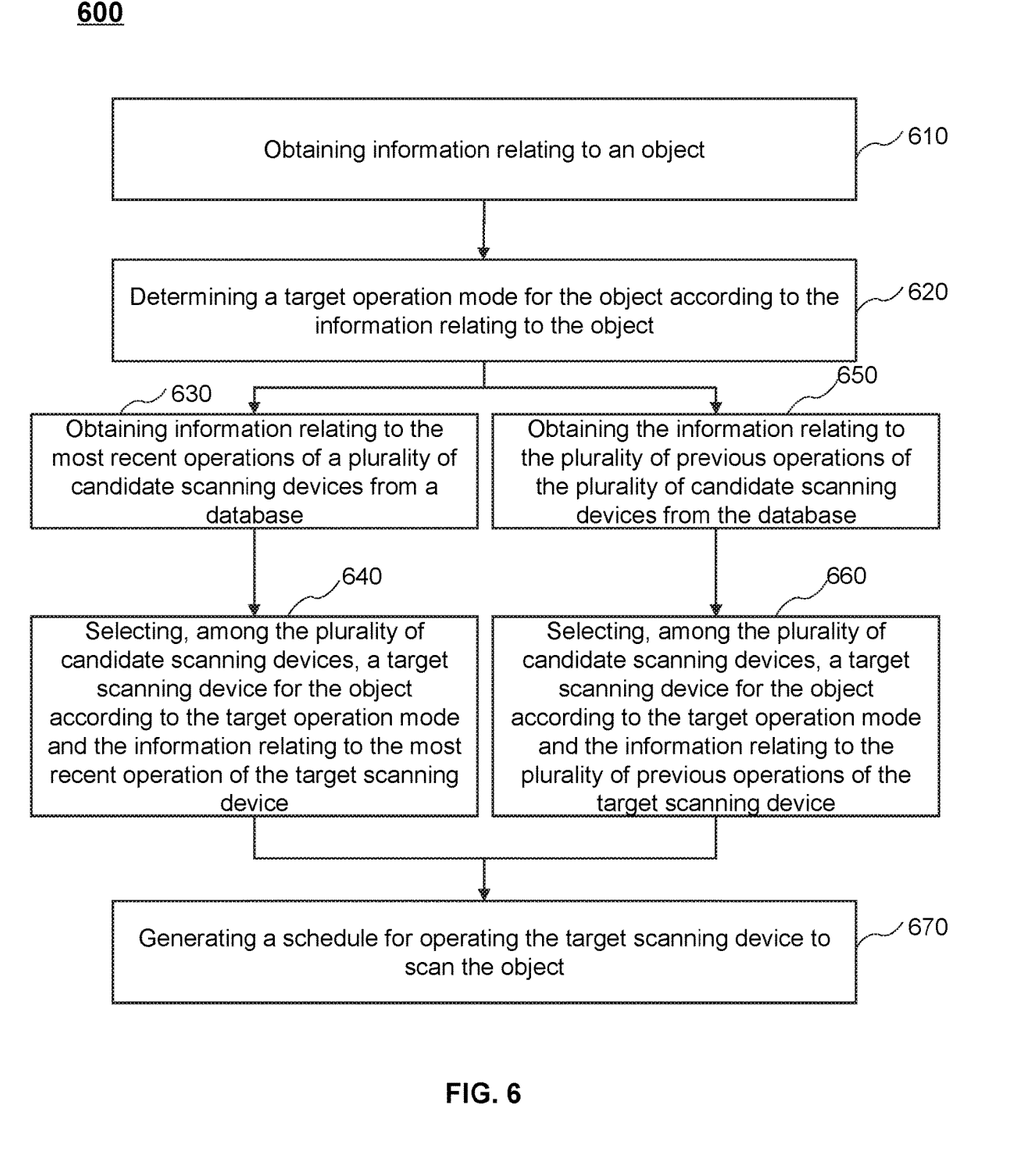
FIG. 6 is a flowchart illustrating an exemplary process for scanning an object according to some embodiments of the present disclosure.

FIG. 6 is a flowchart illustrating an exemplary process 600 for scanning an object according to some embodiments of the present disclosure. In some embodiments, one or more operations of the process 600 illustrated in FIG. 6 may be executed by one or more components of the imaging system 100. For example, the process 600 illustrated in FIG. 6 may be implemented as a set of instructions stored in the storage device 140. The processing engine 120, the processor 220 of the computing device 200 illustrated in FIG. 2, and/or the processor 340 of the mobile device 300 illustrated in FIG. 3 may execute the set of instructions and may accordingly be directed to perform the process 600. For illustration purposes, the implement of the process 600 in the processing engine 120 is described herein as an example, but the process 600 can also be similarly implemented in the processor 220 of the computing device 200 and/or the processor 340 of the mobile device 300. In some embodiments, operation 540 of the process 500 in FIG. 5 may be implemented by performing one or more operations in the process 600.

In 610, the obtaining module 410 may obtain the information relating to an object. Operation 610 may be similar to operation 510 of FIG. 5, and therefore the descriptions thereof are not repeated here.

In 620, the determination module 420 may determine a target operation mode for the object according to the information relating to the object. Operation 620 may be similar to operation 520 of the process 500 illustrated in FIG. 5, and therefore the descriptions thereof are not repeated here.

In 630, the obtaining module 410 may obtain the information relating to the most recent operations of a plurality of candidate scanning devices from a database. A candidate scanning device may be a scanning device (e.g., the scanning device(s) 110) that is capable of performing the scanning of the object. For example, the plurality of candidate scanning devices may be the scanning devices 110-1, 110-2, . . . , 110-*n* as described in connection with FIG. 1.

The most recent operation of a candidate scanning device may refer to the operation that starts at the time closest to the obtaining of the information relating to the object. For example, if no operation is being performed by the candidate scanning device, the last operation completed by the candidate scanning device may be regarded as the most recent operation of the candidate scanning device. As another example, if an operation is being performed by the candidate scanning device, the operation may be regarded as the most recent operation of the candidate scanning device.

The most recent operation may be a CT scanning, a PET scanning, an MRI scanning, a PET-CT scanning, etc. The information relating to the most recent operation of the candidate scanning device may include a specific portion (e.g., a head, a breast, a lung) of an object scanned by the candidate scanning device, a scanning parameter associated with the most recent operation, and/or an image reconstruction parameter associated with the most recent operation. The database storing the information relating to the most recent operations of the plurality of candidate scanning devices may be similar to that described in connection with operation 530, and the descriptions thereof are not repeated.

In 640, the selection module 430 may select, among the plurality of candidate scanning devices, a target scanning device for the object according to the target operation mode and the information relating to the most recent operation of the target scanning device.

For example, the target scanning device may be a candidate scanning device whose most recent operation is consistent with the target operation mode. As the target operation mode relates to the information of the object to be scanned, the selection module 430 may determine a candidate scanning device as the target scanning device if the selection module 430 determines that the candidate scanning device satisfies a certain condition relating to the information of the object. Merely by way of example, the certain condition may include a first condition that the specific portion scanned in the most recent operation performed by the candidate scanning device is the same as the target portion of the object to be scanned, a second condition that a scanning parameter associated with the most recent operation performed by the candidate scanning device is the same as the scanning parameter associated with the scanning to be performed on the object, and/or a third condition that an image reconstruction parameter associated with the most recent operation performed by the candidate scanning device is the same as the image reconstruction parameter associated with the scanning to be performed on the object. In some embodiments, the selection module 430 may determine a candidate scanning device as the target scanning device if the selection module 430 determines that the candidate scanning device satisfies the most amount of the three conditions (e.g., all of the three conditions). In some embodiments, if more than one candidate scanning device satisfies the condition(s) or the most amount of the conditions, the selection module 430 may randomly select a candidate scanning device from the more than one candidate scanning device as the target scanning device. It shall be noted that the description of three conditions with respect to the most recent operation is merely provided for illustration purpose, multiple variations or modifications (e.g., more than three conditions are provided) may be made under the teachings of the present disclosure. However, those variations and modifications do not depart from the scope of the present disclosure.

In 650, the obtaining module 410 may obtain the information relating to the plurality of previous operations of the plurality of candidate scanning devices from the database. The plurality of previous operations of a candidate scanning device may refer to the previous operations that are previously performed by the candidate scanning device before the information relating to the object is obtained in 610.

The plurality of previous operations may include CT scannings, PET scannings, MRI scannings, PET-CT scannings, etc. The information relating to the plurality of previous operations of the candidate scanning device may include specific portions (e.g., heads, breasts, lungs) of objects scanned by the candidate scanning device, scanning parameters associated with the plurality of previous operations performed by the candidate scanning device, and/or image reconstruction parameters associated with the plurality of previous operations performed by the candidate scanning device.

In 660, the selection module 430 may select, among the plurality of candidate scanning devices, a target scanning device for the object according to the target operation mode and the information relating to the plurality of previous operations of the target scanning device.

In some embodiments, for each of the plurality of candidate scanning devices, the selection module 430 may determine the information relating to the most frequent operations among the plurality of previous operations of the corresponding candidate scanning device. The information relating to the most frequent operations performed by a candidate scanning device may include the specific portion scanned in the most frequent operations performed by the candidate scanning device, a scanning parameter associated with the most frequent operations performed by the candidate scanning device, and/or an image reconstruction parameter associated with the most frequent operations performed by the candidate scanning device.

The selection module 430 may determine a candidate scanning device as the target scanning device if the selection module 430 determines that the candidate scanning device satisfies a specific condition relating to the information of the object. Merely by way of example, the specific condition may include a fourth condition that the specific portion scanned in the most frequent operations performed by the candidate scanning device is the same as the target portion of the object to be scanned, a fifth condition that a scanning parameter associated with the most frequent operations performed by the candidate scanning device is the same as the scanning parameter associated with the scanning to be performed on the object, and/or a sixth condition that an image reconstruction parameter associated with the most frequent operations performed by the candidate scanning device is the same as the image reconstruction parameter associated with the scanning to be performed on the object. In some embodiments, the selection module 430 may determine a candidate scanning device as the target scanning device if the selection module 430 determines that the candidate scanning device satisfies the most amount of the three conditions (e.g., all of the three conditions). In some embodiments, if more than one candidate scanning device satisfies the condition(s) or the most amount of the conditions, the selection module 430 may randomly select a candidate scanning device from the more than one candidate scanning device as the target scanning device. It shall be noted that the description of three conditions with respect to the most frequent operation is merely provided for illustration purpose, multiple variations or modifications (e.g., more than three conditions are provided) may be made under the teachings of the present disclosure. However, those variations and modifications do not depart from the scope of the present disclosure.

In 670, the scheduling module 440 may generate a schedule for operating the target scanning device to scan the object. Operation 670 may be similar to operation 550 in FIG. 5, and the description thereof is not repeated here.

It should be noted that the above description of the process 600 is merely provided for illustration, and not intended to limit the scope of the present disclosure. For persons having ordinary skills in the art, multiple variations and modifications may be made to the process 600 under the teachings of the present disclosure. However, those variations and modifications do not depart from the scope of the present disclosure. For example, operation 630 and operation 640 may be optional. As another example, operation 650 and operation 660 may be optional.

Figure 7:
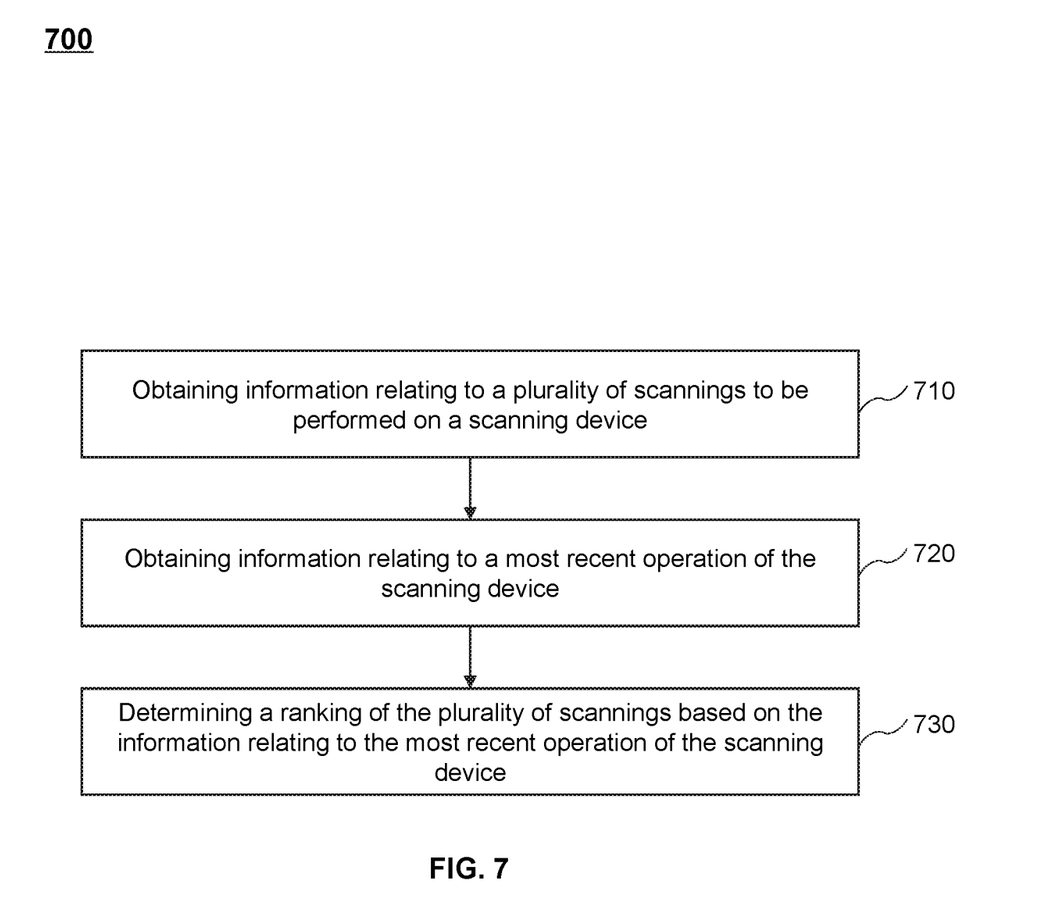
FIG. 7 is a flowchart illustrating an exemplary process for operating a scanning device according to some embodiments of the present disclosure.

FIG. 7 is a flowchart illustrating an exemplary process 700 for operating a scanning device according to some embodiments of the present disclosure. In some embodiments, one or more operations of the process 700 illustrated in FIG. 7 may be executed by one or more components of the imaging system 100. For example, the process 700 illustrated in FIG. 7 may be implemented as a set of instructions stored in the storage device 140. The processing engine 120, the processor 220 of the computing device 200 illustrated in FIG. 2, and/or the processor 340 of the mobile device 300 illustrated in FIG. 3 may execute the set of instructions and may accordingly be directed to perform the process 700. For illustration purposes, the implement of the process 700 in the processing engine 120 is described herein as an example, but the process 700 can also be similarly implemented in the processor 220 of the computing device 200 and/or the processor 340 of the mobile device 300.

In 710, the obtaining module 410 may obtain information relating to a plurality of scannings to be performed by a scanning device. Each of the plurality of scannings may correspond to an object associated with an operation mode as described in connection with, for example, FIG. 5 and FIG. 6. In some embodiments, the obtaining module 410 may obtain the information from the storage device 140, the terminal device(s) 150, or the scanning device(s) 110. In some embodiments, the obtaining module 410 may obtain the information from an RIS that is connected to or communicated with the imaging system 100.

In 720, the obtaining module 410 may obtain information relating to a most recent operation of the scanning device. As described elsewhere in the disclosure, the most recent operation of the scanning device may include information relating to, for example, the specific portion of the object in the most recent operation performed by the scanning device, a scanning parameter associated with the most recent operation performed by the scanning device, and/or an image reconstruction parameter associated with the most recent operation performed by the scanning device.

In 730, the scheduling module 440 may determine a ranking of the plurality of scannings based on the information relating to the most recent operation of the scanning device. The ranking may refer to an order of the plurality of scannings to be performed by the scanning device. In some embodiments, a scanning whose corresponding operation mode is the same as that of the most recent operation of the scanning device may be ranked with the highest priority. For example, the scheduling module 440 may rank a scanning at the first place if the information relating to the object in the scanning matches the most recent operation of the scanning device (e.g., the specific portion to be scanned in the scanning is the same as that of the most recent operation, a scanning parameter associated with the scanning is the same as that of the most recent operation, and/or an image reconstruction parameter associated with the scanning is the same as that of the most recent operation).

In some embodiments, the scheduling module 440 may classify the plurality of scannings to be performed into one or more groups according to the information relating to the plurality of scannings. One or more scannings with similar information relating to the object may be classified into the same group. The scannings belonging to the same group may be consecutively performed such that minimum adjustments of the scanning device (e.g., an adjustment of a scanning parameter) is performed during the plurality of scannings. For example, for a CT system, the scanning device may sequentially perform the scannings that belong to the same group according to a same gantry rotation time (e.g., 0.3 seconds, 3 seconds). The gantry rotation time may refer to the time required to complete one full rotation (360 degrees) of the X-ray tube/detector around the object.

It should be noted that the description of the process 700 is provided for the purposes of illustration, and not intended to limit the scope of the present disclosure. For persons having ordinary skills in the art, various variations and modifications may be conducted under the teaching of the present disclosure. However, those variations and modifications may not depart from the protecting of the present disclosure. For example, operations 710 and 720 may be performed simultaneously. As another example, operation 730 may be omitted, and the plurality of scanning obtained by the obtaining module 410 may be performed by a scanning device according to a same scanning parameter (e.g., the same gantry rotation time).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by the present disclosure and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system comprising:
   a storage device storing executable instructions; and
   at least one processor in communication with the storage device, wherein when executing the executable instructions, the at least one processor is configured to cause the system to:
      obtain information relating to an object;
      determine a target operation mode for the object according to the information relating to the object;
      obtain information relating to previous operations of a plurality of candidate scanning devices from a database, the database storing information relating to operations performed by the plurality of candidate scanning devices;
      select, among the plurality of candidate scanning devices, a target scanning device for the object according to the target operation mode and the information relating to the previous operations of the plurality of candidate scanning devices;
      generate a schedule for operating the target scanning device to scan the object; and
      update, after the target scanning device scans the object, the information relating to operations performed by the target scanning device in the database.

2. The system of claim 1, wherein to determine a target operation mode for the object, the at least one processor is further configured to cause the system to:
   determine the target operation mode based on at least one of a target portion of the object to be scanned, a scanning parameter associated with a scanning to be performed on the object, or an image reconstruction parameter associated with a scanning to be performed on the object.

3. The system of claim 1, wherein the at least one processor is further configured to cause the system to:
   obtain information relating to a most recent operation of each of the plurality of candidate scanning devices; and
   select the target scanning device for the object according to the target operation mode and the information relating to the most recent operation of the target scanning device.

4. The system of claim 1, wherein the at least one processor is further configured to cause the system to:
   obtain information relating to a plurality of previous operations of the plurality of candidate scanning device; and
   select the target scanning device for the object according to the target operation mode and the information relating to the plurality of previous operations of the target scanning device.

5. The system of claim 1, wherein the target operation mode is associated with a CT enhanced scanning or a CT plain scanning.

6. The system of claim 1, wherein the at least one processor is further configured to cause the system to:
   obtain a first plurality of scannings to be performed on the target scanning device, the first plurality of scannings including the scanning to be performed on the object associated with the target operation mode; and
   determine, for the first plurality of scannings, a ranking according to which the target scanning device is configured to perform the first plurality of scannings.

7. The system of claim 6, wherein to determine, for the first plurality of scannings, a ranking, the at least one processor is further configured to cause the system to:
   determine the ranking for the first plurality of scannings based on a most recent operation of the target scanning device.

8. The system of claim 1, wherein at least one of the plurality of candidate scanning devices is configured to perform a second plurality of scannings according to a same gantry rotation time.

9. A method implemented on a computing device including a storage device and a processor, the method comprising:
   obtaining, by the processor, information relating to an object;
   determining, by the processor, a target operation mode for the object according to the information relating to the object;
   obtaining, by the processor, information relating to previous operations of a plurality of candidate scanning devices from a database, the database storing information relating to operations performed by the plurality of candidate scanning devices;
   selecting, by the processor, among the plurality of candidate scanning devices, a target scanning device for the object according to the target operation mode and the information relating to the previous operations of the plurality of candidate scanning devices;
   generating, by the processor, a schedule for operating the target scanning device to scan the object; and updating, by the processor, after the target scanning device scans the object, the information relating to operations performed by the target scanning device in the database.

10. The method of claim 9, wherein determining, by the processor, a target operation mode for the object further comprises:
determining, by the processor, the target operation mode based on at least one of a target portion of the object to be scanned, a scanning parameter associated with a scanning to be performed on the object, or an image reconstruction parameter associated with a scanning to be performed on the object.

11. The method of claim 9, further comprising:
obtaining, by the processor, information relating to most recent operations of the plurality of candidate scanning devices; and
selecting, by the processor, the target scanning device for the object according to the target operation mode and the information relating to the most recent operation of the target scanning device.

12. The method of claim 9, further comprising:
obtaining, by the processor, information relating to a plurality of previous operations of the plurality of candidate scanning device; and
selecting, by the processor, the target scanning device for the object according to the target operation mode and the information relating to the plurality of previous operations of the target scanning device.

13. The method of claim 9, wherein the target operation mode is associated with a CT enhanced scanning or a CT plain scanning.

14. The method of claim 9, further comprising:
obtaining, by the processor, a plurality of scannings to be performed on the target scanning device, the plurality of scannings including the scanning to be performed on the object associated with the target operation mode; and
determining, by the processor, for the plurality of scannings, a ranking according to which the target scanning device is configured to perform the plurality of scannings.

15. The method of claim 14, wherein determining, by the processor, for the plurality of scannings, a ranking further comprises:
determining, by the processor, the ranking for the plurality of scannings based on a most recent operation of the target scanning device.

16. The method of claim 14, wherein the target scanning device is configured to perform the plurality of scannings according to a same gantry rotation time.

17. A non-transitory computer readable medium embodying a computer program product, the computer program product comprising instructions configured to cause a computing device to:
obtain information relating to an object;
determine a target operation mode for the object according to the information relating to the object;
obtain information relating to previous operations of a plurality of candidate scanning devices from a database, the database associating information relating to operations to the plurality of candidate scanning devices;
select, among the plurality of candidate scanning devices, a target scanning device for the object according to the target operation mode and the information relating to the previous operations of the plurality of candidate scanning devices;
generate a schedule for operating the target scanning device to scan the object; and
update, after the target scanning device scans the object, the information relating to operations performed by the target scanning device in the database.

18. The non-transitory computer readable medium of claim 17, wherein to determine a target operation mode for the object, the computer program product is further configured to cause the computing device to:
determine the target operation mode based on at least one of a target portion of the object to be scanned, a scanning parameter associated with a scanning to be performed on the object, or an image reconstruction parameter associated with a scanning to be performed on the object.

19. The non-transitory computer readable medium of claim 17, wherein the computer program product is further configured to cause the computing device to:
obtain information relating to a most recent operation of each of the plurality of candidate scanning devices; and
select the target scanning device for the object according to the target operation mode and the information relating to the most recent operation of the target scanning device.

20. The non-transitory computer readable medium of claim 17, wherein the computer program product is further configured to cause the computing device to:
obtain information relating to a plurality of previous operations of the plurality of candidate scanning device; and
select the target scanning device for the object according to the target operation mode and the information relating to the plurality of previous operations of the target scanning device.

* * * * *